United States Patent
Mauk et al.

(10) Patent No.: US 8,911,938 B2
(45) Date of Patent: Dec. 16, 2014

(54) REACTION CHAMBER HAVING PRE-STORED REAGENTS

(75) Inventors: Michael G. Mauk, Greenville, DE (US); Haim H. Bau, Swarthmore, PA (US); Amanda W. Dyson, Woodlyn, PA (US); Sudhir Ramprasad, Philadelphia, PA (US); Dafeng Chen, Philadelphia, PA (US); Do Young Byun, Seoul (KR)

(73) Assignee: The Trustees Of The University Of Pennsylvania, Philadelphia, PA (US)

( * ) Notice: Subject to any disclaimer, the term of this patent is extended or adjusted under 35 U.S.C. 154(b) by 674 days.

(21) Appl. No.: 12/331,483

(22) Filed: Dec. 10, 2008

(65) Prior Publication Data

US 2009/0226911 A1   Sep. 10, 2009

Related U.S. Application Data

(60) Provisional application No. 61/012,669, filed on Dec. 10, 2007.

(51) Int. Cl.
| | | |
|---|---|---|
| C12Q 1/68 | (2006.01) |
| C12M 1/36 | (2006.01) |
| C12P 19/34 | (2006.01) |
| G01N 33/00 | (2006.01) |
| G01N 31/20 | (2006.01) |
| G01N 35/00 | (2006.01) |

(52) U.S. Cl.
CPC ........ *G01N 31/20* (2013.01); *G01N 2035/0097* (2013.01)
USPC ........ 435/6.1; 435/91.2; 435/287.2; 422/68.1

(58) Field of Classification Search
None
See application file for complete search history.

(56) References Cited

U.S. PATENT DOCUMENTS

| | | | | |
|---|---|---|---|---|
| 5,948,673 | A | * | 9/1999 | Cottingham ............... 435/287.2 |
| 6,143,496 | A | * | 11/2000 | Brown et al. ................ 435/6.11 |
| 6,613,560 | B1 | * | 9/2003 | Tso et al. .................... 435/287.2 |
| 7,604,983 | B2 | * | 10/2009 | O'Keefe et al. ............. 435/287.2 |
| 2004/0208792 | A1 | * | 10/2004 | Linton et al. ..................... 422/99 |
| 2007/0003443 | A1 | * | 1/2007 | Sandell et al. ................ 422/100 |
| 2007/0099290 | A1 | * | 5/2007 | Iida et al. .................... 435/287.2 |
| 2008/0241890 | A1 | * | 10/2008 | Gumbrecht et al. ......... 435/91.2 |

FOREIGN PATENT DOCUMENTS

| | | | |
|---|---|---|---|
| WO | WO 96/00301 | * | 1/1996 |
| WO | WO2005106023 | * | 11/2005 |

* cited by examiner

*Primary Examiner* — Betty Forman
(74) *Attorney, Agent, or Firm* — Baker & Hostetler LLP (57) ABSTRACT

Disclosed are preloaded analysis modules comprising reagents disposed within a barrier material capable of liberating the reagents, at a time advantageous to a reaction scheme, when exposed to certain activation conditions or reagents. Also disclosed are related methods for analyzing samples with such modules.

11 Claims, 6 Drawing Sheets

Schematic

REACTION CHAMBER HAVING PRE-STORED REAGENTS

CROSS-REFERENCE TO RELATED APPLICATIONS

This application claims the benefit of U.S. Application Ser. No. 61/012,669, filed Dec. 10, 2007, the entirety of which is incorporated by reference herein.

STATEMENT OF GOVERNMENT RIGHTS

The U.S. government may have certain rights in the claimed invention. At least a portion of the work underlying the claimed invention was supported by funding from the National Institutes of Health, grant number NIH/NIDCR UO1DE01785.

FIELD OF THE INVENTION

The claimed invention relates to the field of diagnostic devices. The claimed invention also relates to the field of chemical reactors.

BACKGROUND OF THE INVENTION

Many clinical diagnostics and biotechnology processes utilize complex, conditions-sensitive processes. One such process is temperature-sensitive enzymatic amplification of nucleic acids. Such a polymerase chain reaction (PCR) is routinely used to produce multiple copies of sequence-specific nucleic acid molecules in order to facilitate their detection, sequencing, or cloning. For example, viral and bacteria pathogens can be detected in blood and saliva samples by amplifying nucleic acid sequences specific to those pathogens and assaying any amplification product using fluorescence detection. For a wide range of clinical and non-clinical applications, PCR-based assays are considered superior assays.

Compared to immunoassays, however, PCR-based processes are considered tedious, time consuming, prone to contamination, and labor intensive. In PCR-based assays, nucleic acids typically extracted and isolated from cell culture or clinical specimens such as blood, urine or saliva, so that the isolated nucleic acids are in sufficiently pure form to serve as a suitable template for amplification. Moreover, the reagents for the amplification step are labile and must be stored at low temperatures. Just prior to performing the PCR, the reagents are thawed and introduced into the PCR reaction vessel or chamber in precise amounts, along with the nucleic acid template isolated from the sample. Other sensitive assays are also time-consuming and require careful monitoring by trained personnel.

Accordingly, there are numerous assays and techniques in the art that require careful attention to using precise quantities of reagents. Accordingly, there is a need in the art for methods and devices capable of storing metered quantities of reagents for an extended period of time and in a manner that renders the reagents accessible during a chemical reaction with minimum intervention from a user.

SUMMARY OF THE INVENTION

In overcoming the described challenges, the present invention first provides preloaded analysis modules, comprising: a chamber; a barrier material disposed within the chamber, the barrier material being immiscible with aqueous media, the barrier material being capable of being activated so as to release material disposed within the barrier material; and at least one reagent disposed within the barrier material, the at least one reagent being substantially inert to the barrier material.

Also provided are methods for analyzing a sample, comprising: introducing a sample into a chamber comprising one or more reagents disposed within a barrier material, the one or more reagents being essentially inert to the barrier material, the barrier material being inert to aqueous media, and the barrier material being capable of releasing the one or more reagents upon activation; activating the barrier material so as to release one or more reagents; and reacting the one or more reagents with the sample.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings:

FIG. 3 depicts (a) a chamber before pre-loading of reagents, (b) a chamber with a solvent-bonded cap with wax-encapsulated, dry-stored PCR reagents and a membrane;

DETAILED DESCRIPTION OF ILLUSTRATIVE EMBODIMENTS

The present invention may be understood more readily by reference to the following detailed description taken in connection with the accompanying figures and examples, which form a part of this disclosure. It is to be understood that this invention is not limited to the specific devices, methods, applications, conditions or parameters described and/or shown herein, and that the terminology used herein is for the purpose of describing particular embodiments by way of example only and is not intended to be limiting of the claimed invention. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another embodiment includes from the one particular value and/or to the other particular value. Similarly, when values are expressed as approximations, by use of the antecedent "about," it will be understood that the particular value forms another embodiment. All ranges are inclusive and combinable.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any subcombination. Further, reference to values stated in ranges include each and every value within that range.

In one aspect, the present invention discloses preloaded analysis modules, which modules comprise a chamber and a barrier material disposed within the chamber, the barrier material being immiscible with aqueous media, the barrier material being capable of being activated so as to release material disposed within the barrier material; and at least one reagent disposed within the barrier material. The reagent is suitably substantially inert to the barrier material.

The chamber of the disclosed invention is suitably disposed on a substrate. Such chambers may be depressions, trenches, troughs, pits, blisters, or other forms that are manufactured by removing a portion of the substrate. Substrates are suitably a polymer, a metal, a metal oxide, a ceramic, and the like. The material of the substrate may be dictated by the needs of the user and may depend on the chemical reactions that a user wishes to perform. Polycarbonate is considered one suitable substrate material, although other polymers—such as polyethylene—may also be suitable in certain application.

Figure 4:
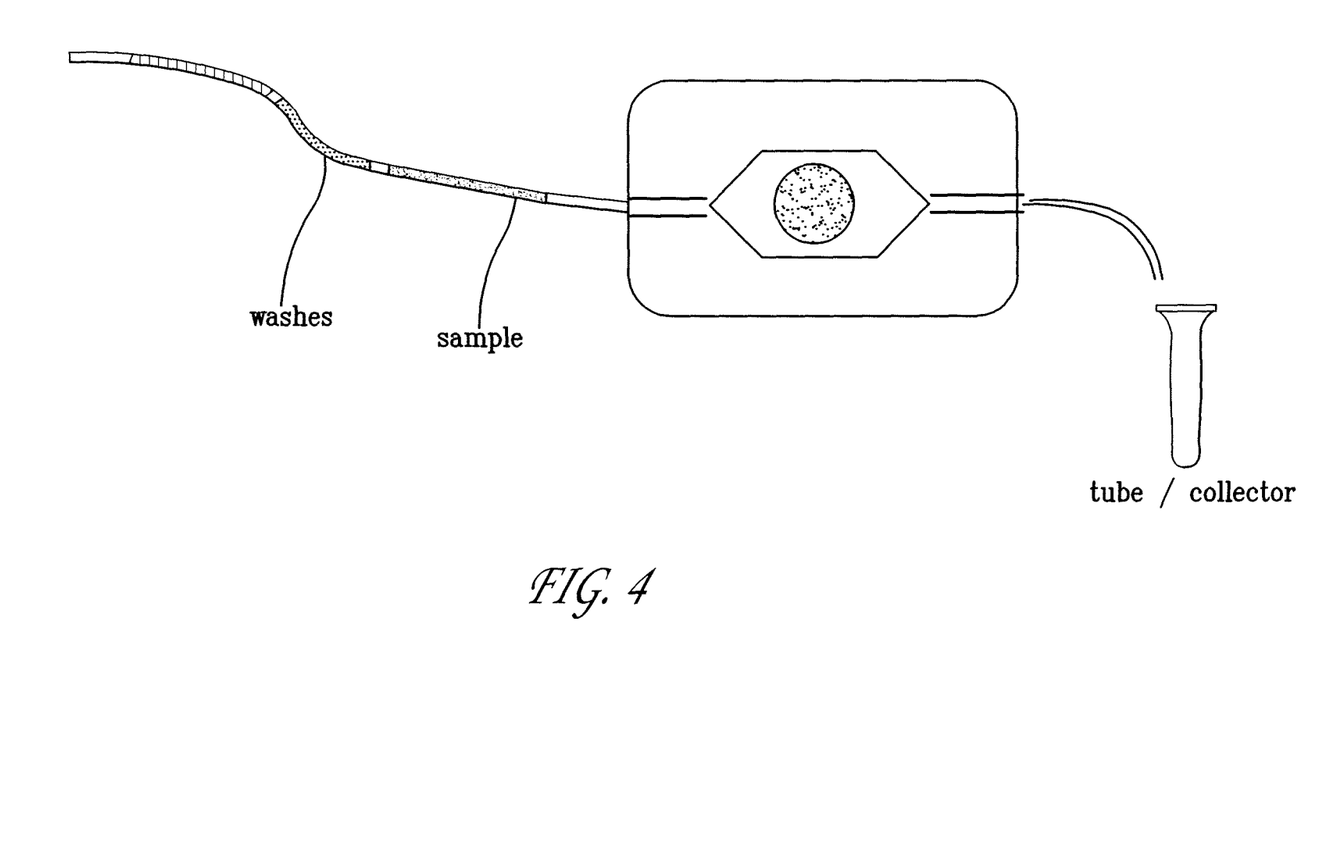
FIG. 4 depicts a chamber connected by inlet and outlet tubes for automated sample loading, washes, and PCR reagent hydration.

Chambers may include one or more inlets, as is shown, for example, in FIG. 4. A chamber may be part of a larger, integrated microfluidic system, in which case the chamber may also have one or more outlets to allow for removal of sample, waste product, buffer, and the like. While chambers may be of a range of different sizes and conformations, it is envisioned that the inlet to a chamber has a cross-sectional dimension in the range of from about 1 to about 10000 microns, or in the range of from about 5 to about 5000 microns, or even in the range of from about 10 to about 100 microns. It is envisioned that outlets are of similar cross-sectional area as the described inlets. Chambers may comprise contemplated volumes in the range of from about 0.1 to about 1000 microliters, or from about 1 to about 100 microliters, or even from about 5 to about 50 microliters. The ultimate size of the chamber will depend on the user's needs. The chamber can be a flow-through chamber, wherein reagents, samples, or other compositions are introduced and removed from the chamber in an ongoing, batch, or semi-batch process. In some embodiments, the chamber is a tank or other container, wherein material introduced to the chamber remains in the chamber until removed by the user. The chamber can be in a horizontal, vertical or any other orientation. In some embodiments, the chamber may be vertically-oriented such that movement of material in and out of the chamber is governed or assisted by gravity.

A chamber may include one or more observation ports that enable visual inspection of at least a portion of the contents of the chamber. Such a port is useful, where, for example, the user has fluorescently labeled one or more species residing within the chamber and desires to monitor the presence of the labeled species. The observation port may be formed directly in the chamber or may be a part of a seal that isolates the interior of the chamber from the external environment. Seals may be formed from a polymer, a rubber, a glass, a metal, and the like. Observation ports may be fashioned from a transparent material, such as a polymer or a glass.

One or more valves may also be included with the chamber. Such valves may be used to modulate fluid flow into, within, and away from the chamber; flaps, butterfly valves, and ball valves are all considered acceptable valve types. The valves may be actuated by an actuator external to the chamber, in turn allowing a user to control fluid flow within the chamber. The chamber may be constructed in such a way that the products of any reactions that take place within the chamber or any barrier material—described elsewhere herein—that is present in the chamber does not occlude the valves. As an example, the chamber may include one or more depressions at the bottom or one or more recesses at the top so as to trap such products or barrier material and prevent such material from floating or flowing into one or move valves.

Figure 1:
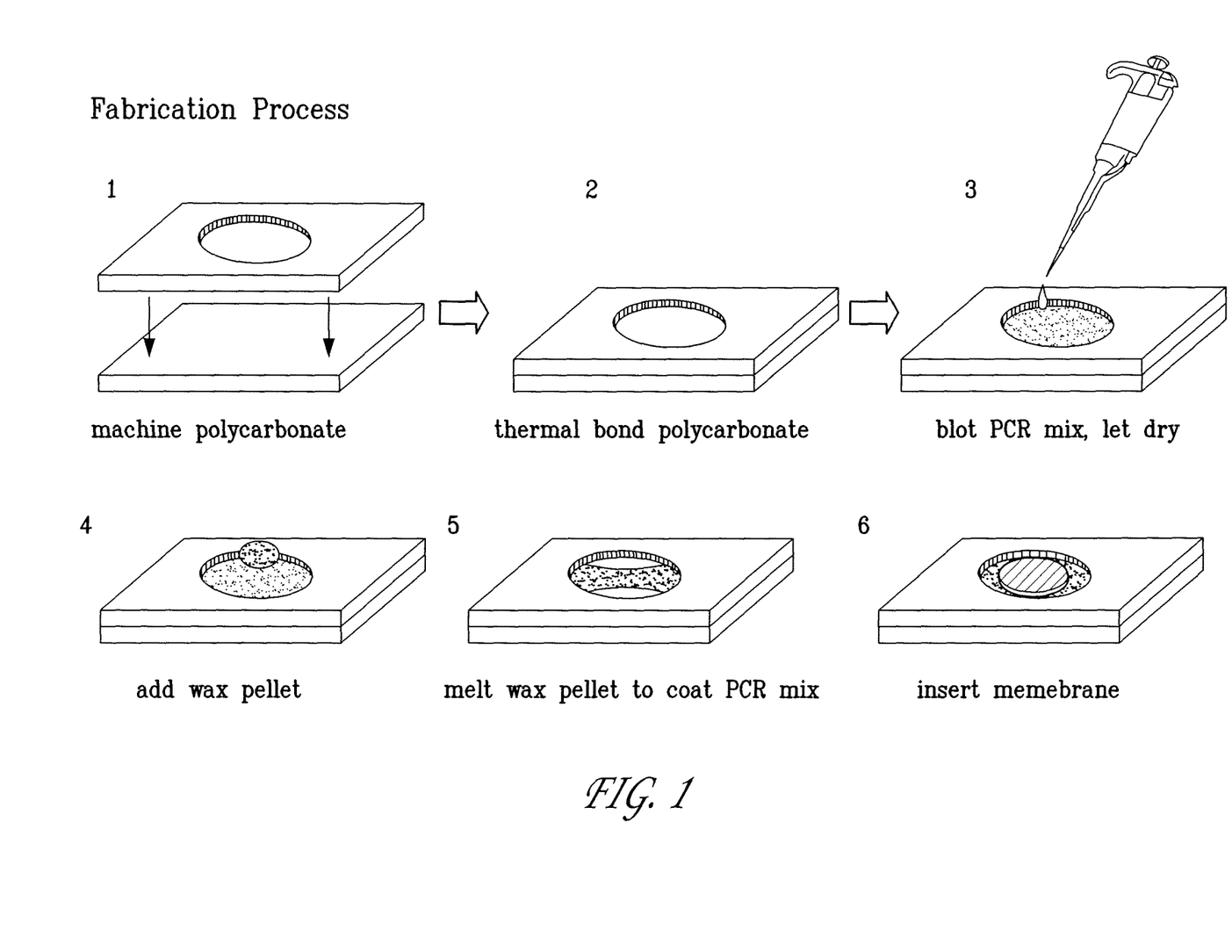
FIG. 1 depicts steps for preparing a chamber for PCR.
Figure 2:
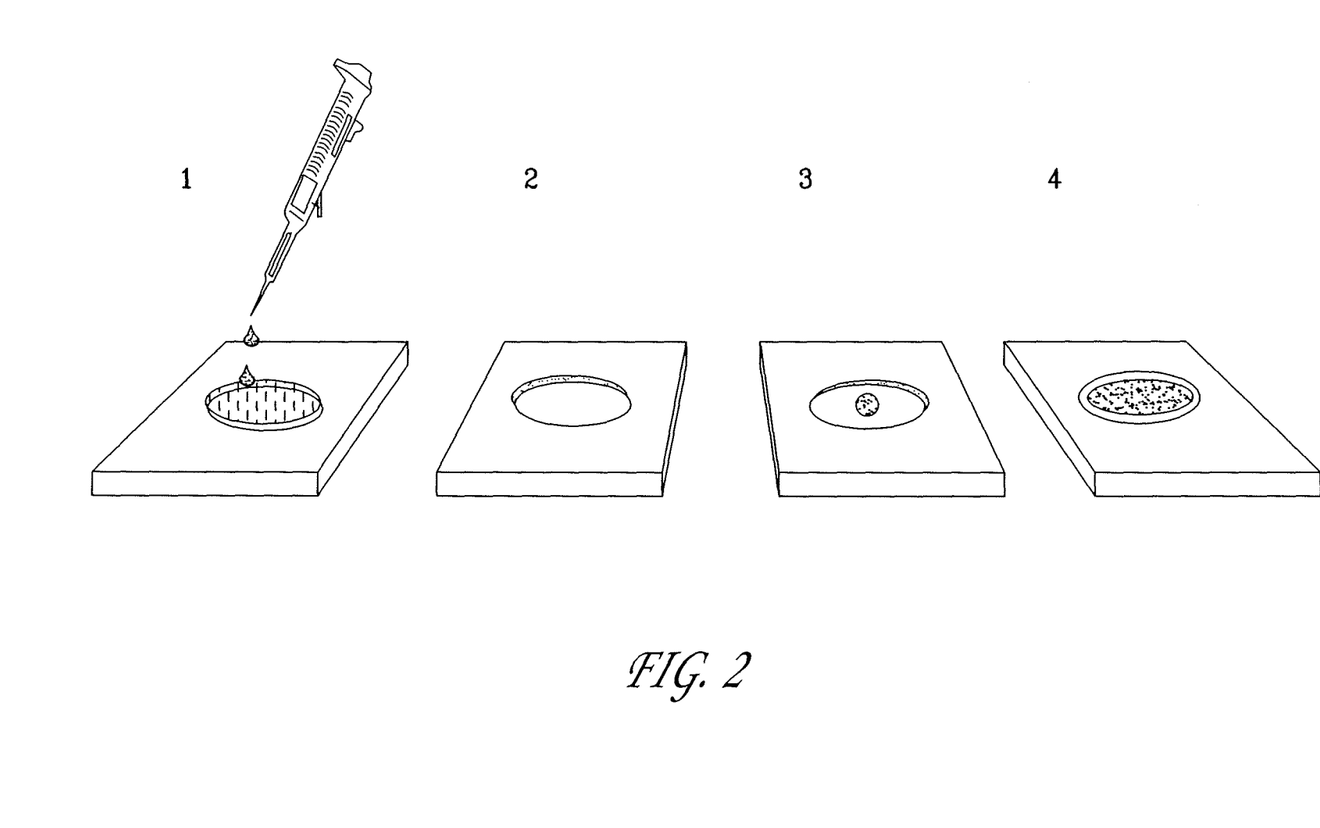
FIG. 2 depicts pre-loading, drying, and wax encapsulation of PCR reagents in a chamber.
Figure 3A:
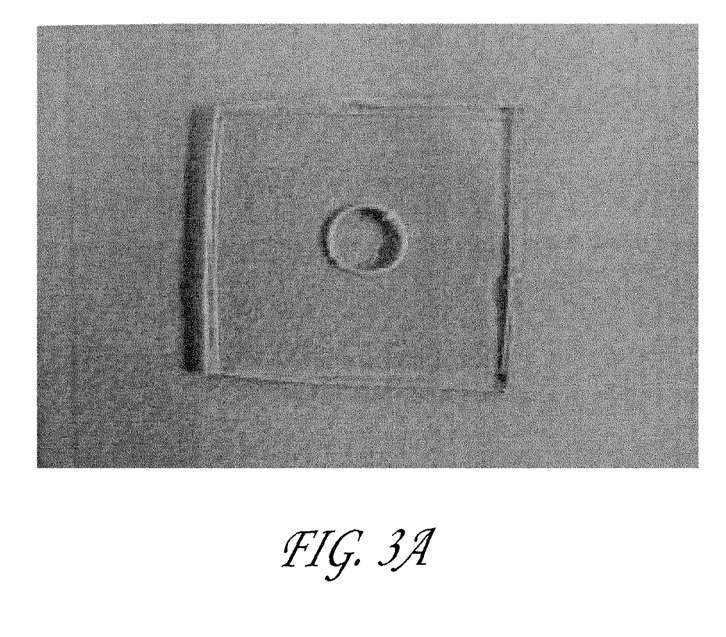
Figure 3B:
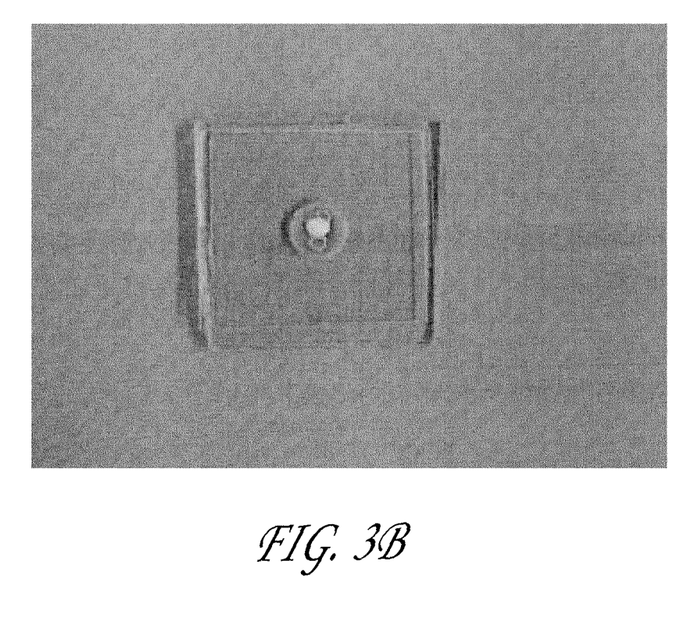

The ability of the barrier material to suitably protect reagents disposed within against an aqueous solution—until the time of activation—is one consideration in choosing a suitable barrier material, which consideration may make hydrophobic materials particularly favorable. The barrier material is suitably, as shown in FIG. 1, disposed on one surface of the chamber. The barrier materials of the claimed invention preferably remain at a fixed location within the chamber when subjected to fluid flow. Fixing the location of the barrier material may be accomplished through natural adhesion of the barrier material to the chamber, or by using an adhesive to affix the barrier material to the chamber.

The barrier material suitably comprises a material that changes phase when heated to greater than ambient temperature, such as a material that melts or even degrades when heated to greater than ambient temperature. Thermoplastic materials are considered suitable barrier materials, and paraffin wax is considered especially suitable. The barrier material may be chosen, at least in part, on the basis of its melting temperature—materials that are stable at ambient conditions but flow when exposed to temperatures that are only moderately greater than ambient conditions are considered especially suitable.

Barrier materials that degrade or otherwise liberate reagents contained within when exposed to ultraviolet light, infrared light, or both, are also considered suitable, as are materials that are capable of degradation upon irradiation. Care is taken to select a barrier material-reagent combination where the method of activating, melting, degrading, or otherwise altering the barrier material so as to liberate reagents contained therein does not also adversely affect the reagents, or, moreover, any chemical reactions that the user seeks to perform using the reagents and a sample introduced into the chamber. As an example, if the user desired to perform a polymerase chain reaction on a sample, care would be taken to select a barrier material that would not, upon liberating the reagents contained within, adversely affect that reaction. Care is suitably taken in choosing a combination of barrier material and reagents that are effectively inert to one another or that will not impair one another's function to an undesirable degree.

Alternatively, a barrier material that becomes at least partially miscible with an aqueous medium upon extended exposure to an aqueous medium may also be suitable, for certain applications. Further, materials that degrade when exposed to one or more chemical degradants may also be suitable; such a degradant may be an acid, a base, an enzyme, or any other species that breaks down the barrier material or changes its phase so as to liberate a reagent contained within the barrier material. Degradants are suitably soluble in aqueous media, but this is not a necessary requirement.

In some embodiments, the barrier material achieves upon activation a density different than that of aqueous media. In such cases, the barrier material may float upwards so as to avoid interference with a reaction proceeding within the chamber; other barriers may maintain or increase their density. Waxes are considered suitable materials for these embodiments.

Reagents suitable for inclusion in the barrier material are suitably dried for incorporation into the barrier material, as shown in FIG. 1. Reagents include an enzyme, a nucleic acid, a nucleic acid primer, a buffer, a salt, a polymer, a deoxyribonucleotide, a monomer, a nucleotide, a biological material, a preservative, a polymer, an initiator, or any combination thereof. Dyes, tags, labels, and the like may also be stored within the barrier material. Agents that can generally be dried and reconstituted by the addition of water or aqueous media are considered particularly suitable.

Suitable enzymes include, for example, Taq polymerase and other polymerases, reverse transcriptase enzymes, and the like. Salts suitable for the claimed invention include KI, $MgCl_2$, and the like. Nucleotides such as dNTPs, where N stands for A, C, G, T, or U nucleotides of nucleic acids RNA and DNA, oligonucleotide primers, carrier DNA and RNA, are all considered includable reagents, as are buffer components, carbohydrate stabilizers such as trehalose, or even polymers such as polethylene glycol.

Dyes may also be used as reagents. Suitable dyes include SYBR Green and other dyes that will be known to the user having ordinary skill in the art and will be chosen according to the user's goals and needs. Passivants—such as bovine serum albumin (BSA)—may also be used as reagents, as well as PCR enhancing-species such as dimethyl sulfoxide (DMSO) and betaine. Commercial preservatives—for example, Biomatrica SAMPLEGARD™ (www.biomatrica.com, San Diego, Calif., USA)—may also be included as reagents.

Lysing agents such as lysozymes and proteinase K may be used as reagents. Other commercial lysing reagents, chaotropic salts such as guanidine HCl, guanidine thiocyanate, NaCl, NaBr, and NaI, sodium perchlorate, and detergents—including such as sodium dodecyl sulfate (SDS) and polysorbate detergents, such as TWEEN™ (www.croda.com, Edison, N.J., USA).

Also provided are methods for analyzing samples. The disclosed methods include introducing a sample into a chamber comprising one or more reagents disposed within a barrier material, the one or more reagents being essentially inert to the barrier material, the barrier material being inert to aqueous media, and the barrier material being capable of releasing the one or more reagents upon activation; activating the barrier material so as to release one or more reagents; and reacting the one or more reagents with the sample.

Suitable chambers are described elsewhere herein. As described, the chamber may be disposed on a substrate.

Introducing the sample can include flowing, dropping, spraying, or any combination thereof. In some embodiments, the sample is flowed from another section of a microfluidic system into the chamber. Samples may reside in an aqueous medium, but may also be present in hydrophobic media and other fluids.

Activating the barrier material is suitably accomplished by heating, irradiating, illuminating, magnetizing, electrifying, sonicating, or any combination thereof, suitable barrier materials include, among other things, paraffins, and are described elsewhere herein. The method of activating the barrier material is suitably chosen so as to minimize any adverse effects on any reagents released or liberated from the barrier material. It is to be observed that the present methods are particularly advantageous where a chemical reaction is optimally performed at a specific temperature above ambient temperature. Where that temperature is at or above the temperature that activates the barrier material and releases a reagent, the reagent thus becomes available to react with the sample at the optimal reaction temperature, thus allowing for a so-called hot-start reaction.

Reacting the sample with the reagent can include contacting the sample and the reagent; suitable reagents are described elsewhere herein. It is envisioned that suitable reactions include polymerizing, binding, neutralizing, acidifying, lysing, de-polymerizing, transfecting, infecting, de-acidifying, annealing, labeling, tagging, binding, amplifying, or any combination thereof. Polymerase chain reactions are considered particularly suitable candidates for the claimed methods, as described elsewhere herein. It will be apparent to those having ordinary skill in the art that other reactions lend themselves to the claimed methods.

The claimed methods also contemplate heating at least a portion of the chamber, cooling at least a portion of the chamber, applying an electric current to at least a portion of the chamber, applying a magnetic field to at least a portion of the chamber, introducing one or more additional fluids into the chamber, introducing one or more additional reagents into the chamber, or combinations thereof. Such additional operations may be necessary to effect the desired reaction or to optimize the desired reaction. The optimal set of operations for a particular reaction or reaction scheme will be known to those having ordinary skill in the art, and may also include closing one or more valves leading into the chamber so as to isolate the chamber's contents during the course of a reaction from fluids and reagents residing outside of the chamber.

The claimed methods also include monitoring the progress of the reacting of the reagents with the sample, which can include monitoring the production of one or more products of the reacting. This may be accomplished by visually inspecting, monitoring an electrical signal, monitoring a chemical property, or any combination thereof. As an example, the user may perform a reaction using such reagents and conditions that the product of the reaction fluoresces under a particular wavelength of light. In such a case, the user may illuminate the contents of the chamber at that wavelength and monitor the increase in fluorescence so as to apprehend the progress of the reaction.

To further described the claimed invention, a particular embodiment is described, which embodiment combines preloading of the PCR reaction chamber with PCR reagents, primers and enzymes in dried form, and encapsulation of the dried PCR components with wax or other materials with similar properties. The combined PCR components are first prepared in correct proportions, as a buffered, aqueous solution. The reaction mixture can be prepared with components at higher concentrations than normally used in PCR by reducing the amount of water added to the mixture. As such, more concentrated PCR mixtures will tend to dry faster. The liquid PCR reagent mixture is then loaded into the PCR vessel or chamber and left to air dry. The drying process can be accelerated by applying mild heat (<50° C.) and/or placing the vessel or chamber under vacuum.

After sufficient dehydration (e.g., 1 to 24 hours) the PCR reagents are dried in the form of film residue or crusty coating covering the inner surfaces of the chamber or vessel. Freeze drying of the PCR reagent mixture is also feasible, in which case the PCR mixture is frozen, by for example, cooling the chamber or vessel with dry ice. The water is removed from the sublimation, which can be accelerated under vacuum. The reagents can also be provided in dry form. A PCR-compatible dye can be added to the mixture to make the residue more visibly evident in the PCR chamber. The dried PCR reagents include the polymerase enzyme, one or more primer pairs, buffers, nucleotides, and other additives that enhance PCR such as bovine serum albumin (BSA) or polyethylene glycol (PEG), as well as various stabilizers and preservatives. The primers are short (20-30 base pair) oligonucleotides that bind to complementary initiate the replication of specific nucleic acid sequences by the polymerase enzyme. Multiplexing of the PCR reaction, i.e., the simultaneous amplification of distinct nucleic acid sequences, can be effected by using multiple primer pairs.

To perform the PCR step, a liquid sample portion containing the nucleic acid template is added to the reaction vessel. The programmed temperature cycling of the PCR process is then initiated, the first step of which heats the reaction mixture to over 90° C., causing the wax encapsulant to melt. Because molten wax is less dense than the aqueous reaction mixture, the immiscible molten wax portion is buoyant and segregates to the top of the reaction mixture. As a result, the dried PCR reagents are exposed to the aqueous phase, and are quickly and completely hydrated by the liquid sample.

When rehydrated for PCR, the PCR components will be at concentrations determined by the original formulation of the mixture dried in the chamber or vessel, and the amount of liquid (containing the nucleic acid template) added to chamber. The volume of liquid used to rehydrate the dried PCR components is limited by the size of the reaction chamber or vessel, and thus, the amount of PCR components dried in the chamber can be scaled to yield a PCR reaction mixture with the optimal concentration of components. In practice, successful PCR amplification can still be achieved even if the final concentration of PCR components varies from 50% to 200% of the nominal optimized concentrations. Thus, the process is not overly sensitive to the amount of liquid that rehydrates the dried PCR mix.

The method described herein has the added advantage of a so-called 'hot start' PCR regimen: the reagents and nucleic acid template are kept separated until the reaction mixture has reached a more optimal temperature. Thus, non-optimal or unwanted reactions that occur at low temperatures due to non-specific primer annealing and spurious amplification are avoided. A second advantage of wax encapsulation is its function as a moisture barrier. Dried PCR reagents tend to be hygroscopic, and absorption of water will decrease the shelf-life of the PCR reagents dried in the chamber. Thus, the encapsulation will facilitate long term storage of the preloaded, dried PCR reagents. While some of the described embodiments address the use of the claimed invention in PCR reactions, the present invention may be applied to other reaction schemes in addition to PCR wherein controlled release of one or more reagents is desirable.

EXAMPLES

Figure 5:
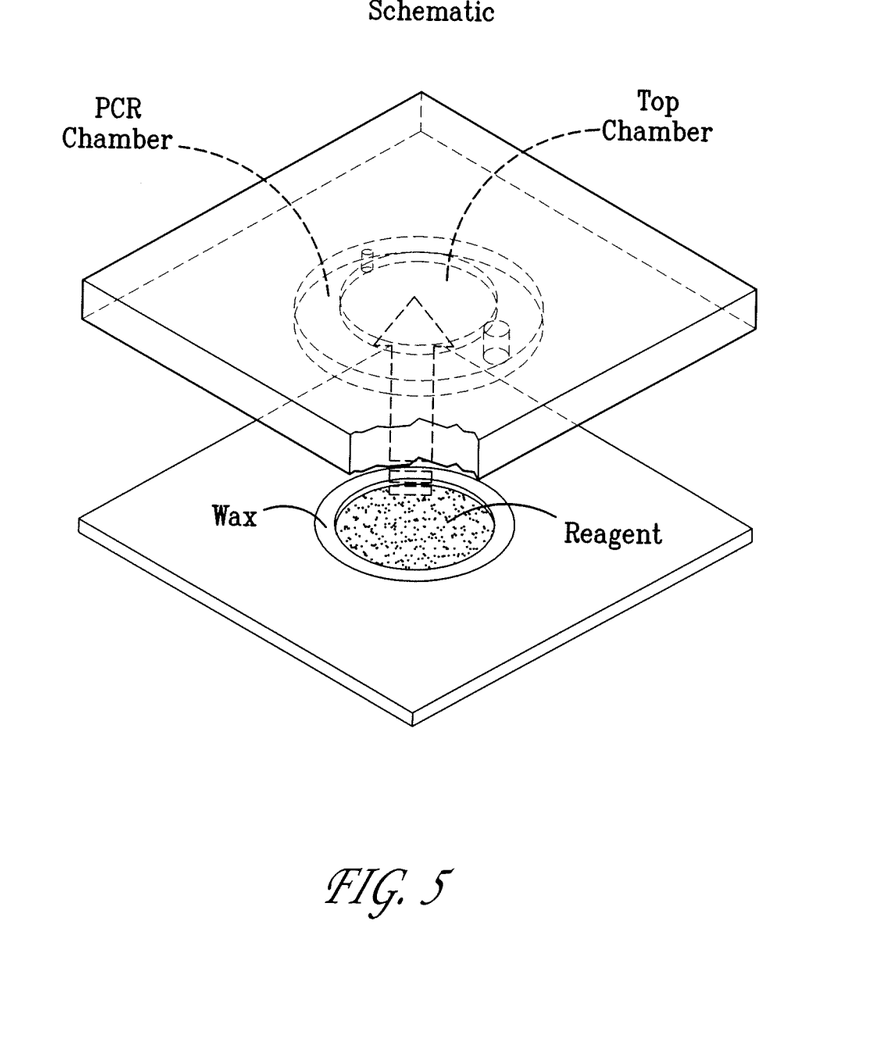
FIG. 5 depicts a schematic view of the assembly of a pre-loaded chamber.
Figure 6:
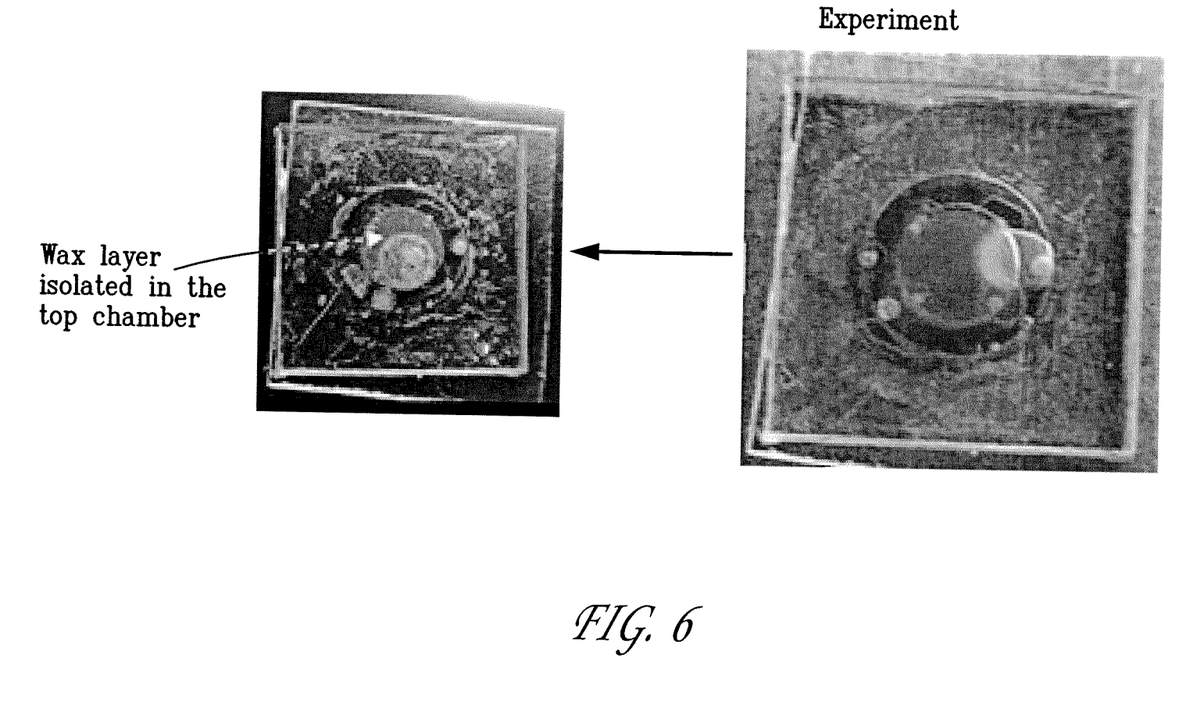
FIG. 6 illustrates a constructed pre-loaded chamber.

This example describes a plastic (polycarbonate) PCR chip that utilizes a single chamber for bacterial cell lysis, nucleic acid isolation, and PCR. FIGS. 1 and 5 show the steps in preparing the chip for operation. PCR reagents (including primers and Taq polymerase) are mixed with a commercial preservative, pre-loaded into the chamber of the chip (unbonded with no cover), and dried as a film coating the inside the chamber. The dried PCR charge is encapsulated with a layer of paraffin wax that protects the PCR mix from dissolution during the lysis and various wash steps.

In another example, dried viruses are placed on the bottom surface of a chamber milled into a substrate. A thermoplastic barrier material—such as paraffin wax—is disposed atop the reagents, and the chamber—having an inlet and an outlet and two valves—is sealed. A cell sample is flowed into the chamber and the wax is heated so as to melt and release the viruses contained within. Additional reagents capable of enhancing the entry of the viruses into the cells are introduced into the chamber via the inlet valve, and the viruses proceed to enter the cells. The outlet valve is opened, and buffer is introduced into the chamber so as to wash the virus-laden cells out of the chamber.

What is claimed:

1. A method for analyzing a sample using a preloaded analysis module, the preloaded analysis module defining a chamber having an inlet and an outlet, the chamber also including one or more recesses in a top surface of the chamber, the preloaded analysis module comprising one or more reagents disposed within a barrier material, the one or more reagents and the barrier material being disposed within the chamber, the one or more reagents being essentially inert to the barrier material, the barrier material being inert to aqueous media, and the barrier material being capable of releasing the one or more reagents upon activation, the method comprising:

introducing a sample into the chamber through the inlet;

activating the barrier material so as to release one or more reagents, wherein the chamber and the barrier material are configured such that when the barrier material is activated, the barrier material floats upward and the one or more recesses traps the barrier material to as to prevent the barrier material from floating or flowing into the outlet;

reacting the one or more reagents react with the sample; and after the reacting step, removing the sample from the chamber through the outlet.

2. The method of claim 1, wherein the chamber is disposed on a substrate.

3. The method of claim 1, wherein the introducing step comprises flowing, dropping, spraying, or any combination thereof of the sample into the chamber through the inlet.

4. The method of claim 1, wherein the step of introducing the sample into the chamber includes introducing the sample disposed in an aqueous medium.

5. The method of claim 1, wherein the activating step comprises heating, irradiating, illuminating, magnetizing, electrifying, sonicating, or any combination thereof.

6. The method of claim 1, wherein the reacting step comprises contacting, polymerizing, binding, neutralizing, acidifying, lysing, de-polymerizing, transfecting, infecting, de-acidifying, annealing, labeling, tagging, binding, amplifying, or any combination thereof.

7. The method of claim 1, wherein the reacting step comprises a polymerase chain reaction.

8. The method of claim 6, further comprising heating at least a portion of the chamber, cooling at least a portion of the chamber, applying an electric current to at least a portion of the chamber, applying a magnetic field to at least a portion of the chamber, introducing one or more additional fluids into the chamber, introducing one or more additional reagents into the chamber, or any combination thereof.

9. The method of claim 1, further comprising a step of monitoring progress of the reacting step.

10. The method of claim 9, wherein the monitoring step comprises monitoring production of one or more products of the reacting step.

11. The method of claim 10, wherein the monitoring step comprises visually inspecting, monitoring an electrical signal, monitoring a chemical property, or any combination thereof.

* * * * *

UNITED STATES PATENT AND TRADEMARK OFFICE
CERTIFICATE OF CORRECTION

| | | |
|---|---|---|
| PATENT NO. | : 8,911,938 B2 | Page 1 of 1 |
| APPLICATION NO. | : 12/331483 | |
| DATED | : December 16, 2014 | |
| INVENTOR(S) | : Michael G. Mauk et al. | |

It is certified that error appears in the above-identified patent and that said Letters Patent is hereby corrected as shown below:

In the Specification

Column 1,
After "STATEMENT OF GOVERNMENT RIGHTS" remove the paragraph at Lines 13-17 in its entirety and replace with the following -- This invention was made with government support under grant number U01 DE014964 awarded by the National Institutes of Health. The government has certain rights in the invention. --

Signed and Sealed this
Fourteenth Day of April, 2015

Michelle K. Lee
*Director of the United States Patent and Trademark Office*